US012597647B2

(12) United States Patent
Hwang et al.

(10) Patent No.: US 12,597,647 B2
(45) Date of Patent: Apr. 7, 2026

(54) GAS ANALYSIS DEVICE

(71) Applicant: LG ENERGY SOLUTION, LTD.,
Seoul (KR)

(72) Inventors: Dongguk Hwang, Daejeon (KR); Nak Hee Choi, Daejeon (KR)

(73) Assignee: LG ENERGY SOLUTION, LTD.,
Seoul (KR)

( * ) Notice: Subject to any disclaimer, the term of this patent is extended or adjusted under 35 U.S.C. 154(b) by 244 days.

(21) Appl. No.: 18/285,233

(22) PCT Filed: Sep. 22, 2022

(86) PCT No.: PCT/KR2022/014169
§ 371 (c)(1),
(2) Date: Sep. 29, 2023

(87) PCT Pub. No.: WO2023/080444
PCT Pub. Date: May 11, 2023

(65) Prior Publication Data
US 2024/0186595 A1　　Jun. 6, 2024

(30) Foreign Application Priority Data
Nov. 4, 2021　(KR) ........................ 10-2021-0150545

(51) Int. Cl.
*G01N 33/00* (2006.01)
*H01M 10/42* (2006.01)
*G01N 1/24* (2006.01)

(52) U.S. Cl.
CPC .... *H01M 10/4285* (2013.01); *G01N 33/0022* (2013.01); *G01N 33/0073* (2013.01); *G01N 2001/242* (2013.01)

(58) Field of Classification Search
CPC ............ H01M 10/4285; H01M 6/5083; G01N 33/0022; G01N 33/0073; G01N 2001/242;
(Continued)

(56) References Cited

U.S. PATENT DOCUMENTS

| 11,650,255 B2 | 5/2023 | Hwang et al. |
| 2011/0239738 A1 | 10/2011 | Bisschops et al. |

(Continued)

FOREIGN PATENT DOCUMENTS

| CN | 102980962 A | 3/2013 |
| CN | 103604897 A | 2/2014 |

(Continued)

OTHER PUBLICATIONS

XP093185424.,(2020), "Operando Gas Chromatography-Mass Spectrometry of Lithium Ion Batteries during Overcharge and Postmortem Analysis", Austrian Institute of Technology, pp. 1-117.

*Primary Examiner* — Robert R Raevis
(74) *Attorney, Agent, or Firm* — Bryan Cave Leighton Paisner LLP

(57) ABSTRACT

A gas analysis device which is capable of analyzing a gas generated from a secondary battery at high resolution in real time. The gas analysis device comprises a diffusion chamber unit, a plurality of gas analysis units, an injector unit selectively injecting the gas generated from the secondary battery into one of the plurality of gas analysis units, and a control unit.

12 Claims, 4 Drawing Sheets

(58) Field of Classification Search
CPC .......... G01N 1/2226; G01N 2030/202; G01N
30/24; G01N 30/6043; G01N 30/88;
G01N 2030/201; G01N 33/0021; G01N
2001/2229; G01N 2001/2241; G01N
33/0009; G01N 33/004; Y02E 60/10
USPC ............. 73/19.01, 19.02, 23.2, 23.35–23.37,
73/23.39–23.42, 863, 863.01, 863.21,
73/863.31, 863.81, 863.83, 864, 864.34,
73/864.81; 136/190; 205/657, 776
See application file for complete search history.

(56) References Cited

U.S. PATENT DOCUMENTS

| | | | |
|---|---|---|---|
| 2018/0151931 A1 * | 5/2018 | Ko | H01M 12/06 |
| 2018/0284082 A1 | 10/2018 | Jung et al. | |
| 2018/0299414 A1 | 10/2018 | Jung et al. | |
| 2020/0256921 A1 | 8/2020 | Hwang et al. | |

FOREIGN PATENT DOCUMENTS

| | | | | | |
|---|---|---|---|---|---|
| CN | 106053667 | A | | 10/2016 | |
| CN | 106153431 | A | | 11/2016 | |
| CN | 207366443 | U | | 5/2018 | |
| CN | 107743734 | B | * | 9/2023 | |
| JP | 2012511150 | A | | 5/2012 | |
| JP | 2017-090225 | A | | 5/2017 | |
| JP | 2018-515770 | A | | 6/2018 | |
| JP | 2021501316 | A | | 11/2021 | |
| KR | 10-2009-0069360 | A | | 7/2009 | |
| KR | 20120115835 | A | * | 10/2012 | ........... H01M 10/48 |
| KR | 10-2013-0067417 | A | | 6/2013 | |
| KR | 10-2015-0032034 | A | | 3/2015 | |
| KR | 10-1545155 | B1 | | 8/2015 | |
| KR | 10-2016-0066909 | A | | 6/2016 | |
| KR | 10-2051696 | B1 | | 12/2019 | |
| KR | 10-2020-0084530 | A | | 7/2020 | |
| KR | 10-2207519 | B1 | | 1/2021 | |
| KR | 102254111 | B1 | * | 5/2021 | ........... H01M 10/48 |

* cited by examiner

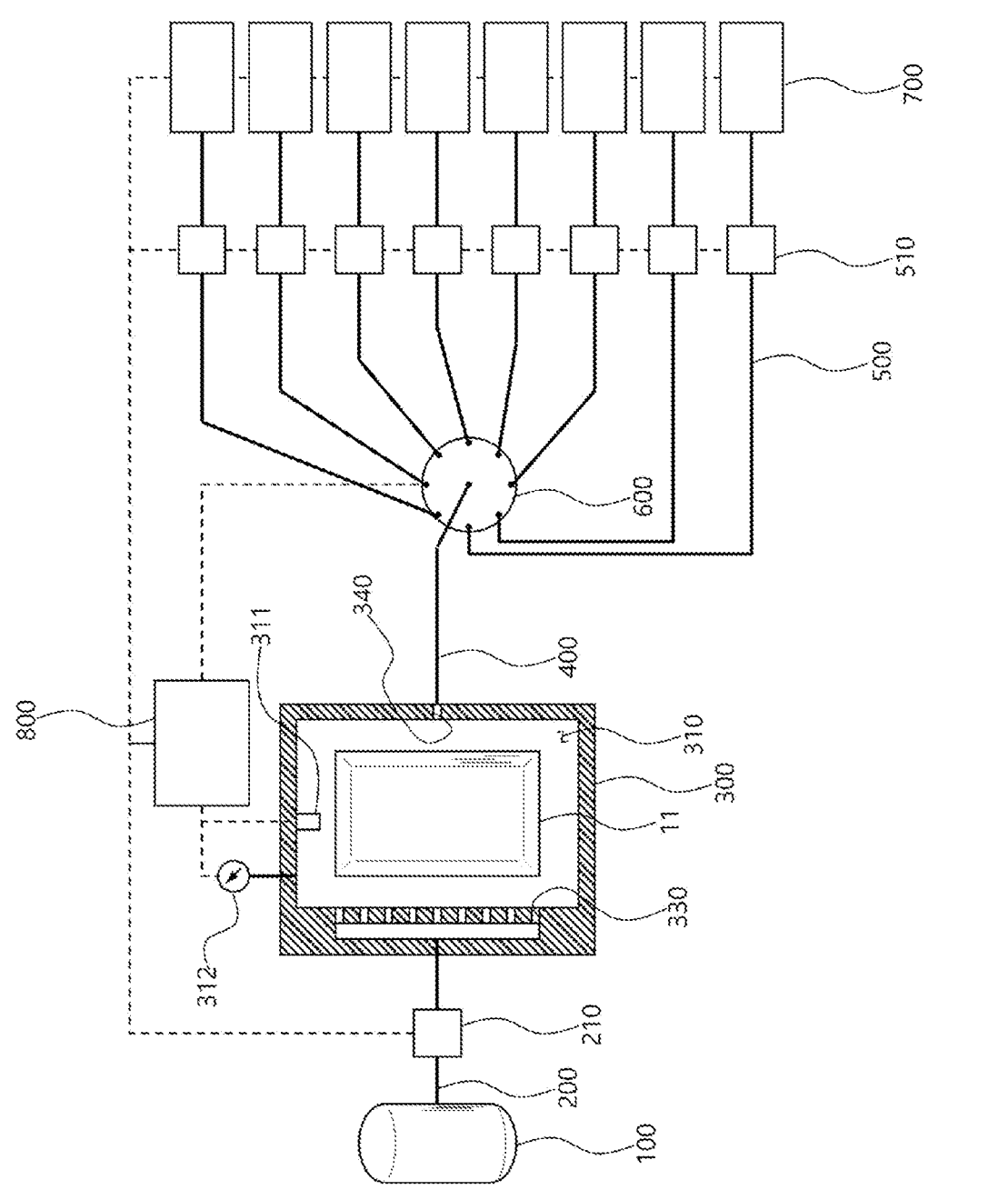
[Fig. 1]

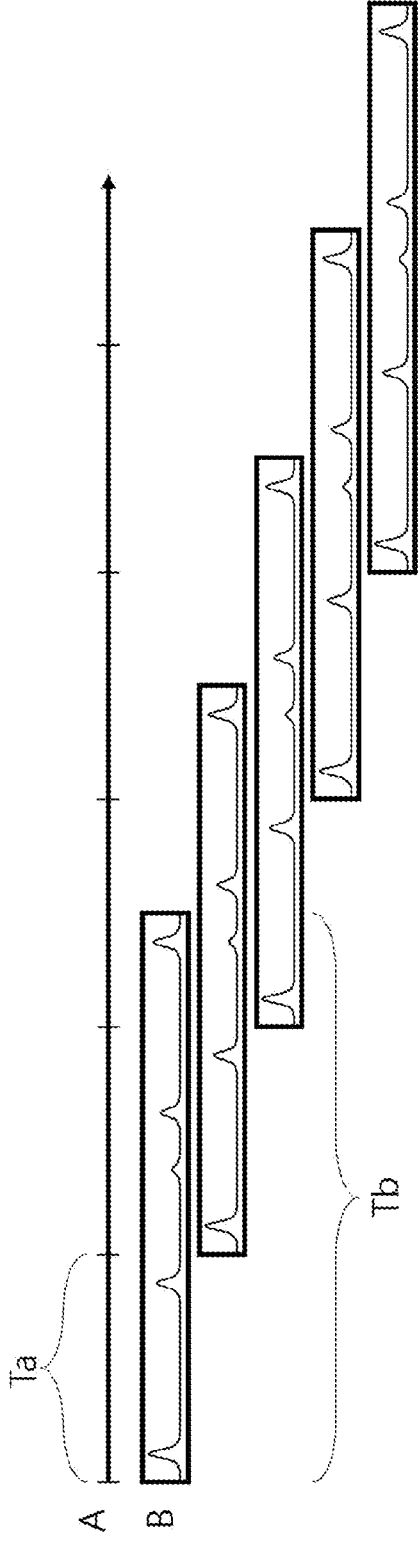
[Fig. 2]

[Fig. 3]
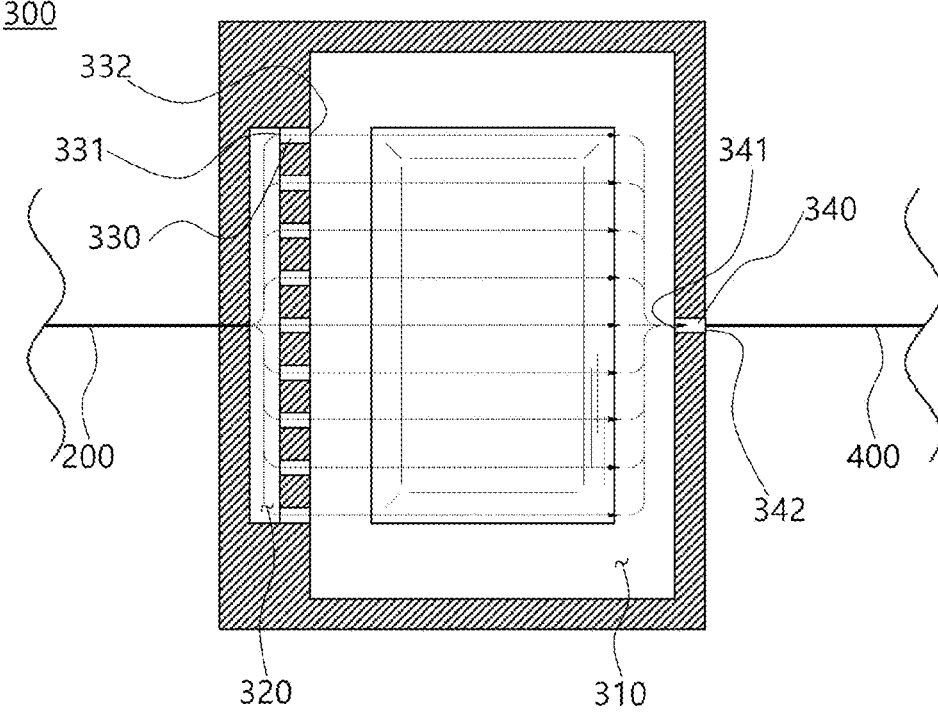
[Fig. 4]
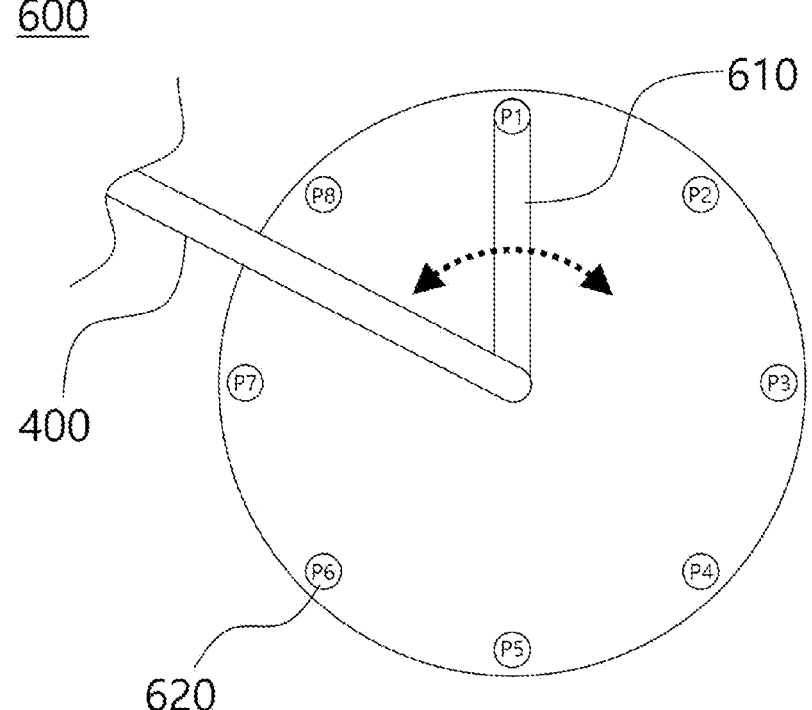

[Fig. 5]
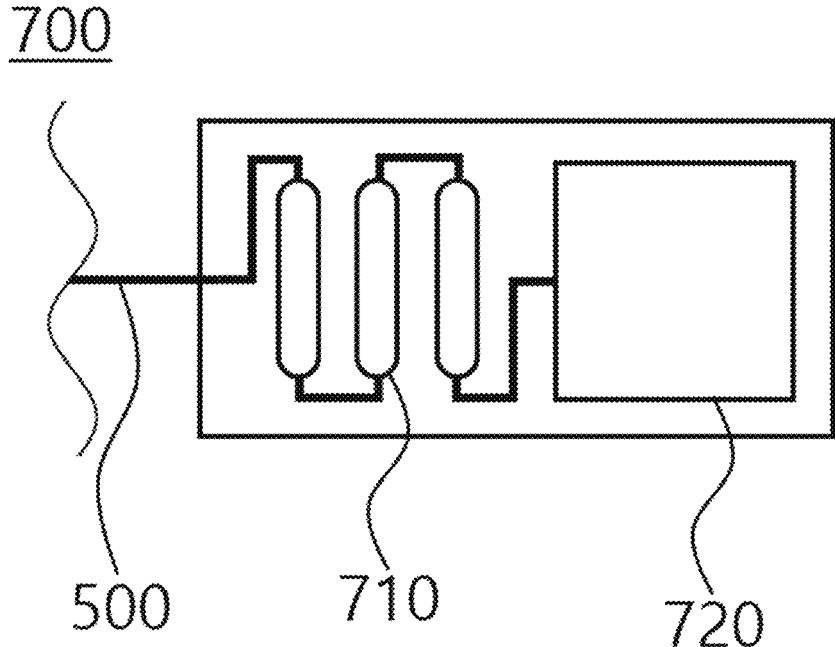
[Fig. 6]
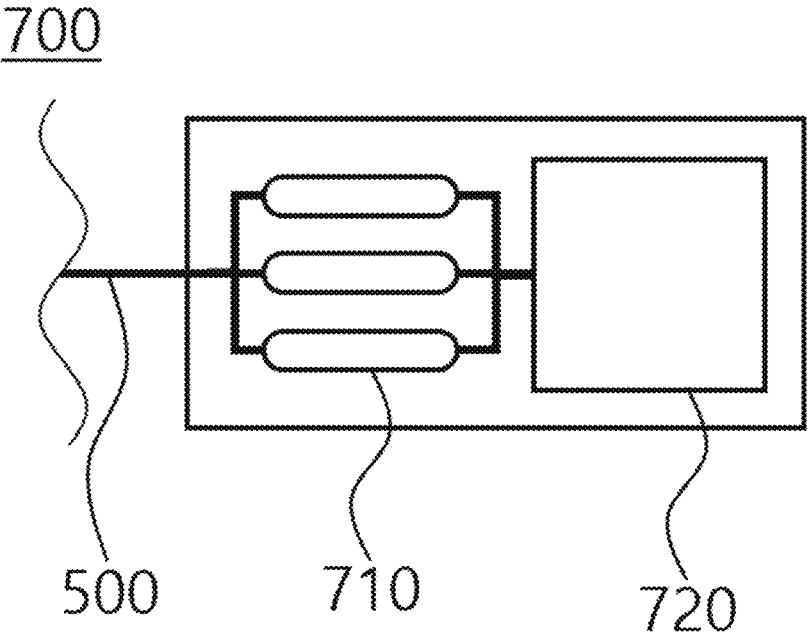

GAS ANALYSIS DEVICE

CROSS-REFERENCE TO RELATED APPLICATIONS

This application is a National Stage Application of International Application No. PCT/KR2022/014169 filed on Sep. 22, 2022, which claims the benefit of priority based on Korean patent application No. 10-2021-0150545 filed on Nov. 4, 2021, the entire disclosure of which is incorporated herein by reference.

FIELD OF DISCLOSURE

The present disclosure relates to a gas analysis apparatus, and relates to a gas analysis apparatus capable of real-time analysis of a gas generated from a secondary battery with high resolution.

BACKGROUND

In general, a secondary battery is a battery that can be used repeatedly through a process of discharging and charging in the reverse direction of converting chemical energy into electrical energy, and the types include a nickel-cadmium (Ni—Cd) battery, a nickel-hydrogen (Ni-MH) battery, a lithium-metal battery, a lithium-ion (Li-ion) battery and a lithium-ion polymer battery, etc. Among these secondary batteries, lithium secondary batteries with high energy density and voltage, long cycle life, and low self-discharge rate have been commercialized and widely used.

Depending on the reaction inside the lithium secondary battery, various types of gases, such as hydrogen, oxygen, nitrogen, carbon monoxide, carbon dioxide, $C_nH_{2n-2}$ (n=2~5), $C_nH_{2n}$ (n=2~5), $C_nH_{2n+2}$ (n=1~5) hydrocarbons and other organic gases, may be generated as gases generated from the secondary battery.

In addition, the lithium secondary battery degrades while generating a large amount of secondary battery generated gas due to electrolyte decomposition according to the repeated charge and discharge progress, and this aspect appears differently depending on the design and use form of the battery. Therefore, it is essential to infer the degradation mechanism of a battery by analyzing the gas generated from the secondary battery during the battery development process.

Therefore, it is very important to accurately analyze the gas generated from the secondary battery. Specifically, information on the composition and content of the gas generated from the secondary battery is useful in the development of battery materials, optimization of battery manufacturing processes, and identification of causes of battery failures. For this, it is important to develop technology to analyze gases generated from the secondary battery.

Analysis of the gas generated from the secondary battery can be performed by transferring the gas generated in the secondary battery to a gas detector such as GC-MS (Gas Chromatography-Mass Spectrometry), GC-TCD (Gas Chromatography-Thermal Conductivity Detector), GC-FID (Gas Chromatography-Flame Ionization Detector), etc.

For example, GC-MS may use a column including a stationary phase to separate and inject each gas species with a time difference into a detector, in the operation of a mass spectrometer (MS) as a detector, in order to solve that each compound is decomposed and the molecular weight and mass value of the compound do not match, and the characteristic mass value overlaps in the case of some gas species.

Therefore, in analyzing the gas generated from the secondary battery generated in the secondary battery in real time, the time resolution of the measurement data was determined by the time required for separation and analysis of the gas in the gas detector. In general, the time required for separation and analysis of gas in a gas detector was several minutes to several tens of minutes, limiting high-resolution analysis.

SUMMARY

The present disclosure relates to a gas analysis apparatus, and relates to a gas analysis apparatus capable of real-time analysis of a gas generated from a secondary battery with high resolution.

The technical problems to be achieved by the present disclosure are not limited to the technical problems mentioned above, and other technical problems not mentioned will be clearly understood by those skilled in the art from the following description.

Technical Solutions

A gas analysis apparatus of the present disclosure may include:

a diffusion chamber unit comprising a gas diffusion space which accommodates a secondary battery;

a plurality of gas analysis units receiving a gas generated from the secondary battery from the gas diffusion space of the diffusion chamber unit and analyzing the same;

a gas discharge pipe connected to the diffusion chamber unit to discharge the gas generated from the secondary battery in the gas diffusion space;

a plurality of gas injection pipes provided in the plurality of gas analysis units, respectively;

an injector unit for selectively connecting the gas discharge pipe with one of the plurality of gas injection pipes to inject the gas generated from the secondary battery in the gas diffusion space into one of the plurality of gas analysis units;

a carrier gas supply unit supplying a carrier gas to the gas diffusion space; and a control unit controlling the injector unit.

Advantageous Effects

A gas analysis apparatus of the present disclosure is capable of high-resolution analysis over time in analyzing the gas generated from the secondary battery in real time, and the behavior of the secondary battery according to changes in experimental conditions such as temperature and charging and discharging behavior may be precisely analyzed.

The gas analysis apparatus of the present disclosure is capable of real-time and high-resolution analysis of the variable secondary battery driving environment and conditions, and may enable development of battery materials, optimization of battery manufacturing processes, and identification of the cause of battery failure by simulating the actual secondary battery driving conditions.

BRIEF DESCRIPTION OF DRAWINGS

FIG. 1 is a conceptual diagram illustrating a gas analysis apparatus of the present disclosure.

FIG. 2 is a graph illustrating a time resolution for analysis in a gas analysis apparatus of the present disclosure.

FIG. 3 is a conceptual diagram illustrating a flow of gas in a diffusion chamber unit.

FIG. 4 is a conceptual diagram illustrating an injector unit.

FIG. 5 is a block diagram illustrating a gas analysis unit.

FIG. 6 is a block diagram illustrating another embodiment of a gas analysis unit.

BEST MODE FOR CARRYING OUT THE INVENTION

A gas analysis apparatus of the present disclosure may include:

a diffusion chamber unit comprising a gas diffusion space which accommodates a secondary battery;

a plurality of gas analysis units receiving a gas generated from the secondary battery from the gas diffusion space of the diffusion chamber unit and analyzing the same;

a gas discharge pipe connected to the diffusion chamber unit to discharge the gas generated from the secondary battery in the gas diffusion space;

a plurality of gas injection pipes provided in the plurality of gas analysis units, respectively;

an injector unit for selectively connecting the gas discharge pipe with one of the plurality of gas injection pipes to inject the gas generated from the secondary battery in the gas diffusion space into one of the plurality of gas analysis units;

a carrier gas supply unit for supplying a carrier gas to the gas diffusion space; and a control unit for controlling the injector unit.

In the gas analysis apparatus of the present disclosure, the gas analysis apparatus comprises a carrier gas supply flow path connecting the carrier gas supply unit and the diffusion chamber unit, and the carrier gas supply flow path may comprise a mass flow controller (MFC).

In the gas analysis apparatus of the present disclosure, the diffusion chamber unit may include an inlet through which the carrier gas is injected into the gas diffusion space, and an outlet from which the gas generated from the secondary battery in the gas diffusion space is discharged, wherein an exit of the inlet and an entrance of the outlet may be located on two inner walls facing each other, respectively, among inner walls of the diffusion chamber unit forming the gas diffusion space.

In the gas analysis apparatus of the present disclosure, the diffusion chamber unit may comprise a carrier gas dispersion space to which the carrier gas supply flow path is connected; and a plurality of the inlets, wherein entrances of the plurality of inlets may be connected to the carrier gas dispersion space.

In the gas analysis apparatus of the present disclosure, the secondary battery may be disposed between exits of the plurality of inlets and the entrance of the outlet, and the exit of the plurality of inlets may face one side of the secondary battery.

In the gas analysis apparatus of the present disclosure, the injector unit may be a multi position valve.

In the gas analysis apparatus of the present disclosure, the control unit may receive analysis unit state information from each of the plurality of gas analysis units, and the control unit may control the injector unit based on the analysis unit state information.

In the gas analysis apparatus of the present disclosure, the control unit may include a timer, and the control unit may control the injector unit at a predetermined time period.

The gas analysis apparatus of the present disclosure may further include a plurality of gas sampling units provided respectively in the plurality of gas injection pipes to quantify an amount of the gas generated from the secondary battery injected into each of the plurality of gas analysis units.

In the gas analysis apparatus of the present disclosure, the diffusion chamber unit may comprise a temperature sensor or a pressure sensor, and the control unit may control the injector unit based on a measured value of the temperature sensor or a measured value of the pressure sensor.

In the gas analysis apparatus of the present disclosure, each of the plurality of gas sampling units may comprise a gas sampling space for quantifying the amount of the gas generated from the secondary battery, a volume of the gas sampling space may be formed differently for each of the plurality of gas sampling units, and the control unit may select the gas injection pipe connected to the gas discharge pipe in consideration of the measured value of the temperature sensor, the measured value of the pressure sensor, and the volume of the gas sampling space.

In the gas analysis apparatus of the present disclosure, each of the plurality of gas analysis units may comprise at least two types of columns for decomposing the gas generated from the secondary battery.

DETAILED DESCRIPTION

Hereinafter, with reference to the accompanying drawings, embodiments according to the present disclosure will be described in detail. In this process, the size or shape of the components shown in the drawings may be exaggerated for clarity and convenience of description. In addition, in consideration of the configuration and operation of the present disclosure, specially defined terms may vary depending on the intentions or practices of users and operators. Definitions of these terms should be based on the content throughout this specification.

In the description of the present disclosure, it should be noted that orientation or positional relationship indicated by the terms "center", "top", "bottom", "left", "right", "vertical", "horizontal", "inside", "outside", "one side", "other side", etc, are based on the orientation or positional relationship shown in the drawings, or the orientation or positional relationship that is usually placed when using the product of the present disclosure, and are intended only for explanation and brief description of the present disclosure, and are not to be construed as limiting the present disclosure as they do not suggest or imply that the device or element shown must necessarily be configured or operated in a specific orientation.

FIG. 1 is a conceptual diagram illustrating a gas analysis apparatus of the present disclosure. FIG. 2 is a graph illustrating a time resolution for analysis in a gas analysis apparatus of the present disclosure. FIG. 3 is a conceptual diagram illustrating a flow of gas in a diffusion chamber unit 300. FIG. 4 is a conceptual diagram illustrating an injector unit 600. FIG. 5 is a block diagram illustrating a gas analysis unit 700. FIG. 6 is a block diagram illustrating another embodiment of a gas analysis unit 700.

Hereinafter, with reference to FIGS. 1 to 6, the gas analysis apparatus of the present disclosure is described in detail.

The gas analysis apparatus of the present disclosure may be capable of high-resolution analysis over time in analyzing the gas generated from the secondary battery in real time, and behaviors of a secondary battery 11 according to changes in experimental conditions such as temperature and charging and discharging behavior may be precisely analyzed.

As shown in FIG. 1, the gas analysis apparatus of the present disclosure may include:

the diffusion chamber unit 300 comprising a gas diffusion space 310 which accommodates a secondary battery;

a plurality of gas analysis units 700 receiving a gas generated from the secondary battery 11 from the gas diffusion space 310 of the diffusion chamber unit 300 and analyzing the same;

a gas discharge pipe 400 connected to the diffusion chamber unit 300 to discharge the gas generated from the secondary battery in the gas diffusion space 310;

a plurality of gas injection pipes 500 provided in the plurality of gas analysis units 700, respectively;

the injector unit 600 for selectively connecting the gas discharge pipe 400 with one of the plurality of gas injection pipes 500 to inject the gas generated from the secondary battery in the gas diffusion space 310 into one of the plurality of gas analysis units 700;

a carrier gas supply unit 100 for supplying a carrier gas to the gas diffusion space 310; and a control unit 800 for controlling the injector unit 600.

To analyze the gas generated from the secondary battery 11 in real time is to deliver the gas generated from the secondary battery in the diffusion chamber unit 300 to the gas analysis unit 700 every specific time period under continuous conditions or environments over a long time.

In FIG. 2, graph A represents a time axis, and graph B shows gas analysis results output from a plurality of gas analysis units 700. As shown in FIG. 2, the time period Ta for high resolution analysis of the behavior of the secondary battery 11 over time is generally shorter than the time Tb required for one analysis in one gas analysis unit 700. The gas analysis apparatus of the present disclosure may provide a plurality of gas analysis units 700 to analyze the continuous situation of the secondary battery 11 in a short period of time.

The carrier gas supply unit 100 may supply the carrier gas for transporting the gas generated from the secondary battery located in the gas diffusion space 310 of the diffusion chamber unit 300 to the gas analysis unit 700. The carrier gas may be an inert gas such as helium or the like. The carrier gas supply unit 100 may be a cylinder, a bomb, a gas tank, and the like in which the carrier gas is stored.

The carrier gas supply unit 100 and the diffusion chamber unit 300 may be connected to a carrier gas supply flow path 200. The carrier gas supply flow path 200 may be a pipe or tube through which gas can flow. The carrier gas supplied from the carrier gas supply unit 100 via the carrier gas supply flow path 200 may be supplied to the gas diffusion space 310 of the diffusion chamber unit 300.

A mass flow controller (MFC) 210 may be provided in the carrier gas supply flow path 200 connecting the carrier gas supply unit 100 and the diffusion chamber unit 300. The form of gas delivered from the diffusion chamber unit 300 to the gas analysis unit 700 may be a gas in which a carrier gas and a gas generated from the secondary battery are mixed. Therefore, it is necessary to know the exact amount of carrier gas injected into the gas diffusion space 310 to calculate the amount of the gas generated from the secondary battery 11 through the analysis result output from the gas analysis unit 700. To this end, the carrier gas supply flow path 200 may comprise a mass flow controller 210 for weighing or controlling the amount of carrier gas injected into the gas diffusion space 310.

As shown in FIG. 3, the diffusion chamber unit 300 may include an inlet 330 through which the carrier gas is injected into the gas diffusion space 310, and an outlet 340 through which the gas generated from the secondary battery in the gas diffusion space 310 is discharged.

The diffusion chamber unit 300 may comprise a gas diffusion space 310, which accommodates the secondary battery 11, inside thereof, and the exit 332 of the inlet 330 and the entrance 341 of the outlet 340 may be located on two inner walls facing each other, respectively, among inner walls of the diffusion chamber unit 300 forming the gas diffusion space 310. In other words, the exit 332 of the inlet 330 is formed on one inner wall forming the gas diffusion space 310, and the entrance 341 of the outlet 340 may be formed on the other inner wall forming the gas diffusion space 310.

The carrier gas may be input to the entrance 331 of the inlet 330 and the carrier gas may be supplied to the gas diffusion space 310 through the exit 332 of the inlet 330. The carrier gas and the gas generated from the secondary battery in the gas diffusion space 310 are discharged to the entrance 341 of the outlet 340, and the exit 342 of the outlet 340 is connected to the gas discharge pipe 400 so that the carrier gas and the gas generated from the secondary battery passing through the outlet 340 may be delivered to the gas analysis unit 700.

The diffusion chamber unit 300 may comprise a carrier gas dispersion space 320 to which the carrier gas supply flow path 200 is connected, and the inlet 330 may be provided in plurality, and entrances 331 of the plurality of inlets 330 may be connected to the carrier gas dispersion space 320.

In other words, inside the diffusion chamber unit 300, a gas diffusion space 310 and a carrier gas dispersion space 320, which are divided into each other, are provided, respectively, and the two spaces may be connected through a plurality of inlets 330. Specifically, the entrance 331 of the inlet 330 may be located in the carrier gas dispersion space 320, and the exit 332 of the inlet 330 may be located in the gas diffusion space 310. The carrier gas supply path 200 may be connected to the carrier gas dispersion space 320, so that the carrier gas supplied from the carrier gas supply unit 100 may be supplied to the gas diffusion space 310 through the carrier gas dispersion space 320.

The inlet 330 may be provided in plurality, and the carrier gas may be injected into the gas diffusion space 310 to be uniformly sprayed on the front of the secondary battery 11. The gas analysis apparatus of the present disclosure is performed in real time, and when the carrier gas is intensively injected into the local area in the gas diffusion space 310, the carrier gas and the gas generated from the secondary battery are not sufficiently mixed, which may affect the analysis result. In order to prevent this, a plurality of the inlets 330 may be provided to inject the carrier gas into the gas diffusion space 310 at a uniform density.

Specifically, the secondary battery 11 may be disposed between the exits 332 of the plurality of inlets 330 and the entrance 341 of the outlet 340, and the exits 332 of the plurality of inlets 330 may face one side of the secondary battery 11. Therefore, the carrier gas flows as shown in the dotted arrow shown in FIG. 3, and the carrier gas can uniformly scan the secondary battery 11.

In the gas diffusion space 310 of the diffusion chamber unit 300, a heater (not shown) for heating the secondary battery 11, a charge and discharge module (not shown) for charging and discharging the secondary battery 11, and the like may be provided.

The gas discharge pipe 400 and the plurality of gas injection pipes 500 may be pipes or tubes through which gas can flow. The gas discharge pipe 400 and the plurality of gas injection pipes 500 may be connected to the injector unit 600.

The injector unit 600 may be a multi position valve.

As shown in FIG. 4, the injector unit 600 includes a plurality of ports 620 to which a plurality of gas inlet tubes 500 are connected, and a switching path 610 that is selectively connected to one of the plurality of ports 620 620. The switching flow path 610 may be connected to the gas discharge pipe 400 at one end at the center of the virtual circle. The switching flow path 610 may be a flow path extending in the diametrical direction of the imaginary circle and rotatable with the center of the virtual circle as a rotation axis. In the arc of the virtual circle, a plurality of ports 620 to which the plurality of gas injection tubes 500 are connected may be arranged. The switching flow path 610 may be selectively connected to the port 620 of one of the plurality of ports 620 while rotating, whereby the gas discharge pipe 400 may be selectively connected to the gas injection pipe 500 of one of the plurality of gas injection pipes 500.

The control unit 800 may receive analysis unit state information from each of the plurality of gas analysis units 700, and the control unit 800 may control the injector unit 600 based on the analysis unit state information.

The analysis unit state information is information indicating the state of the gas analysis unit 700, for example, may be information indicating whether the gas analysis unit 700 is analyzing or in a analysis preparation complete state. The analysis preparation complete state may be a state where analysis can start immediately when the gas generated from the secondary battery is injected. For example, the control unit 800 may control the injector unit 600 so that the gas injection pipe 500 connected to the gas analysis unit 700 in the analysis preparation complete state and the gas discharge pipe 400 are connected.

The control unit 800 may include a timer, and the control unit 800 may control the injector unit 600 at a predetermined time period. For example, the control unit 800 may control the injector unit 600 so that the gas injection pipe 500 connected to the gas analysis unit 700 in the analysis preparation complete state and the gas discharge pipe 400 are connected, every predetermined time period.

The control unit 800 is an arithmetic device and may be a device in which hardware and software are combined.

As shown in FIG. 1, a plurality of gas sampling units 510 provided respectively in the plurality of gas injection pipes 500 to quantify the amount of gas generated from the secondary battery injected into each of the plurality of gas analysis units 700 may be further included. The gas sampling unit 510 may be a loop-shaped pipe or tube. The gas generated from the secondary battery can be quantified by the magnitude of the volume of the gas sampling space formed inside the gas sampling unit 510.

The diffusion chamber unit 300 comprises a temperature sensor 311 and a pressure sensor 312, and the control unit 800 may control the injector unit 600 based on a measured value of the temperature sensor 311 or a measured value of the pressure sensor 312.

Specifically, a gas sampling space for quantifying the amount of the gas generated from the secondary battery is provided in each of the plurality of gas sampling units 510, the volume of the gas sampling space is formed differently for each of the plurality of gas sampling units 510, and the control unit 800 may select the gas injection pipe 500 connected to the gas discharge pipe 400 considering the measured value of the temperature sensor 311, the measured value of the pressure sensor 312, and the volume of the gas sampling space. Depending on temperature and pressure, the amount of gas per unit volume (mass, moles, etc.) may vary. Therefore, in order to secure a certain level of detection sensitivity, it is necessary to adjust the amount of gas sampled in the gas sampling unit 510. Therefore, the control unit 800 may control the injector unit 600 so that a gas sampling unit 510 having an appropriate volume of gas sampling space according to the temperature and pressure and a gas analysis unit 700 connected to the gas sampling unit 510 are connected to the gas discharge pipe 400 via a gas injection pipe 500.

As shown in FIGS. 5 and 6, the gas analysis unit 700 may include a column 710 for gas chromatography (GC), and a mass spectrometry (MS), a thermal conductivity detector (TCD), and a flame ionization detector (FID) as a detector 720 for gas detection. The gas generated from the secondary battery delivered to the gas analysis unit 700 may be decomposed while passing through the column 710 and then injected into the detector 720.

Each of the plurality of gas analysis units 700 may have two or more types of columns 710 for decomposing the gas generated from the secondary battery. The type of column 710 for GC may be classified according to a stationary phase filling method, filling material and specification, and the like. For each type of column 710 that varies depending on the stationary phase filling method, filling material, and specification, the time required for the separation of individual components included in the gas generated from the secondary battery may vary. Therefore, by simultaneously using multiple types of columns 710, the gas analysis apparatus of the present disclosure can save time required for GC, and finally, by reducing the time corresponding to the Tb indicated in FIG. 2, a high resolution gas analysis may be possible with a smaller number of gas analysis units 700. In other words, the column 710 may be provided in plurality, and each column may have different conditions of one or more of a stationary phase filling method, filling material, and specification. For example, the column 710 may be provided in three, one column 710 may be provided in a packed manner, the other column 710 may be provided in a micro-packed manner, and the other may be provided in a capillary manner. As another example, the column 710 may be provided in three, one column 710 may be filled with silica substituted with an alkyl group of various lengths or benzene as the filling material, the other column 710 may be filled with polyacrylamide as the filling material, and the other may be filled with agarose or dextrin as the filling material.

The stationary phase filling method means a method of decomposition of the material to be analyzed in the column 710, and may include a packed method, a micro-packed method, a capillary method, and the like.

The filling material means a material filled into the column 710, and may include silica substituted with an alkyl group of various lengths or benzene, polyacrylamide, agarose or dextrin.

The specification may mean the size or shape of the column 710.

Multiple types of columns 710 may be connected in series as shown in FIG. 5 and may be connected in parallel as shown in FIG. 6. For example, the column 710 may be provided in three types.

Although embodiments according to the present disclosure have been described above, these are merely exemplary, and those skilled in the art will understand that various modifications and embodiments of equivalent range are possible therefrom. Therefore, the true technical protection scope of the present disclosure should be defined by the following claims.

DESCRIPTION OF REFERENCE NUMERALS

11 . . . Secondary battery
100 . . . Carrier gas supply unit
200 . . . Carrier gas supply flow path
210 . . . Mass flow controller
300 . . . Diffusion chamber unit
310 . . . Gas diffusion space
311 . . . Temperature sensor
312 . . . Pressure sensor
320 . . . Carrier gas dispersion space
330 . . . Inlet
331 . . . Entrance of inlet
332 . . . Exit of inlet
340 . . . Outlet
341 . . . Entrance of outlet
342 . . . Exit of outlet
400 . . . Gas discharge pipe
500 . . . Gas injection pipe
510 . . . Gas sampling unit
600 . . . Injector unit
610 . . . Switching flow path
620 . . . Port
700 . . . Gas analysis unit
710 . . . Column
720 . . . Detector
800 . . . Control Unit A gas analysis apparatus of the present disclosure is capable of high-resolution analysis over time in analyzing the gas generated from the secondary battery in real time, and the behavior of the secondary battery according to changes in experimental conditions such as temperature and charging and discharging behavior may be precisely analyzed.

The gas analysis apparatus of the present disclosure is capable of real-time and high-resolution analysis of the variable secondary battery driving environment and conditions, and may enable development of battery materials, optimization of battery manufacturing processes, and identification of the cause of battery failure by simulating the actual secondary battery driving conditions.

The invention claimed is:
1. A gas analysis apparatus comprising:
a diffusion chamber unit comprising a gas diffusion space which accommodates a secondary battery;
a plurality of gas analysis units for receiving a gas generated from the secondary battery from the gas diffusion space of the diffusion chamber unit and analyzing the same;
a gas discharge pipe connected to the diffusion chamber unit to discharge the gas generated from the secondary battery in the gas diffusion space;
a plurality of gas injection pipes provided in the plurality of gas analysis units, respectively;

an injector unit for selectively connecting the gas discharge pipe with one of the plurality of gas injection pipes to inject the gas generated from the secondary battery in the gas diffusion space into one of the plurality of gas analysis units;
a carrier gas supply unit for supplying a carrier gas to the gas diffusion space, wherein the gas analysis apparatus comprises a carrier gas supply flow path connecting the carrier gas supply unit and the diffusion chamber unit; and
a control unit for controlling the injector unit.

2. The gas analysis apparatus of claim 1, wherein the carrier gas supply flow path comprises a mass flow controller (MFC).

3. The gas analysis apparatus of claim 2, wherein the diffusion chamber unit comprises:
an inlet through which the carrier gas is injected into the gas diffusion space; and
an outlet from which the gas generated from the secondary battery in the gas diffusion space is discharged,
wherein an exit of the inlet and an entrance of the outlet are located on two inner walls facing each other, respectively, among inner walls of the diffusion chamber unit forming the gas diffusion space.

4. The gas analysis apparatus of claim 3, wherein the diffusion chamber unit comprises:
a carrier gas dispersion space to which the carrier gas supply flow path is connected; and
a plurality of the inlets,
wherein entrances of the plurality of inlets are connected to the carrier gas dispersion space.

5. The gas analysis apparatus of claim 4, wherein the secondary battery is disposed between exits of the plurality of inlets and the entrance of the outlet, and
the exits of the plurality of inlets face one side of the secondary battery.

6. The gas analysis apparatus of claim 1, wherein the injector unit is a multi position valve.

7. The gas analysis apparatus of claim 1, wherein the control unit receives analysis unit state information from each of the plurality of gas analysis units, and
the control unit controls the injector unit based on the analysis unit state information.

8. The gas analysis apparatus of claim 1, wherein the control unit comprises a timer, and
the control unit controls the injector unit at a predetermined time period.

9. The gas analysis apparatus of claim 1, wherein the gas analysis apparatus further comprises a plurality of gas sampling units provided respectively in the plurality of gas injection pipes, wherein the gas analysis apparatus is configured to sample an amount of the gas generated from the secondary battery injected into each of the plurality of gas analysis units based on a volume of the gas sampling units.

10. The gas analysis apparatus of claim 9, wherein the diffusion chamber unit comprises a temperature sensor or a pressure sensor, and
the control unit controls the injector unit based on a measured value of the temperature sensor or a measured value of the pressure sensor.

11. The gas analysis apparatus of claim 10, wherein each of the plurality of gas sampling units comprises a gas sampling space for sampling the amount of the gas generated from the secondary battery,
wherein a volume of the gas sampling space is formed differently for each of the plurality of gas sampling units, and wherein the control unit selects the gas injection pipe connected to the gas discharge pipe in consideration of the measured value of the temperature sensor, the measured value of the pressure sensor, and the volume of the gas sampling space.

12. The gas analysis apparatus of claim 1, wherein each of the plurality of gas analysis units comprises at least two types of columns for-decomposing separating the gas generated from the secondary battery.

* * * * *